(12) United States Patent
Lee et al.

(10) Patent No.: US 9,301,944 B2
(45) Date of Patent: Apr. 5, 2016

(54) METHOD FOR TREATING HEPATITIS C

(71) Applicant: INDUSTRIAL TECHNOLOGY RESEARCH INSTITUTE, Hsinchu County (TW)

(72) Inventors: Lain-Tze Lee, Hsinchu (TW); Shau-Feng Chang, Hsinchu (TW); Cheng Lin, Fengyuan (TW); Shao-Chan Yin, Tainan (TW); Shu-Jiau Chiou, Hsinchu (TW)

(73) Assignee: INDUSTRIAL TECHNOLOGY RESEARCH INSTITUTE, Hsinchu County (TW)

( * ) Notice: Subject to any disclaimer, the term of this patent is extended or adjusted under 35 U.S.C. 154(b) by 142 days.

(21) Appl. No.: 13/681,397

(22) Filed: Nov. 19, 2012

(65) Prior Publication Data

US 2013/0150435 A1    Jun. 13, 2013

Related U.S. Application Data

(63) Continuation-in-part of application No. 12/647,496, filed on Dec. 27, 2009, now abandoned.

(30) Foreign Application Priority Data

Dec. 30, 2008    (TW) .................................. 97151394 A

(51) Int. Cl.
*A61K 31/353* (2006.01)
*A61K 36/87* (2006.01)
*A61K 36/704* (2006.01)

(52) U.S. Cl.
CPC ............. *A61K 31/353* (2013.01); *A61K 36/704* (2013.01); *A61K 36/87* (2013.01)

(58) Field of Classification Search
None
See application file for complete search history.

(56) References Cited

U.S. PATENT DOCUMENTS

| 2003/0078231 A1 | 4/2003 | Wilburn |
| 2006/0216362 A1 | 9/2006 | Enoki et al. |
| 2008/0014331 A1 | 1/2008 | Badalov |

FOREIGN PATENT DOCUMENTS

| CN | 1506361 A | 6/2004 |
| JP | 2003-026584 A | 1/2003 |
| TW | I274551 | 3/2007 |

OTHER PUBLICATIONS

Yang et al. in Journal of Ethnopharmacology, 19, 103-110 (1987).*
Yabe et al. in Phytomedicine 7(6), 493-498 (2000).*
Poynard et al. in The Lancet; 349:825-32 (1997).*

Ubillas et al., "SP-303, An Antiviral Oligomeric Proanthocyanidin from the Latex of Croton lechleri (Sangre de Drago)", Phytomedicine vol. 1 (1994), pp. 77-106.
Tomobe et al., "Modulation of infection-induced inflammation and locomotive deficit and longevity in senescence-accelerated mice-prone (SAMP8) model by the oligomerized polyphenol oligonol", Biomedicine & Pharmacotherapy, 61 (2007), 427-434.
Zhang et al., "Study on the antiviral activities of condensed Tannin of Artemisia Annua L", Natural Product Research and Development, vol. 16, No. 4 (2004), 307-311.
First Office Action issued by the China Intellectual Property Office on Jan. 27, 2011, for the referenced application's counterpart application in China (Appl. No. 200910006596.5).
Notice of Allowance issued by the China Intellectual Property Office on Jul. 13, 2012, for the referenced application's counterpart application in China (Appl. No. 200910006596.5).
Yabe et al., "Ampelopsis brevipedunculata (Vitaceae) extract inhibits a progression of carbon tetrachloride-induced hepatic injury in the mice", Phytomedicine, vol. 7(6), pp. 493-498 (2000).
Office Action (Notification of Examination Opinion) issued by the Taiwan Intellectual Property Office on Mar. 22, 2013, for the above-referenced application's counterpart application in Taiwan (Application No. 097151394).
Sun et al., "Isolation and purification of dimeric and trimeric procyandins from grape seeds", Journal of Chromatography A, 841 (1999)115-121.

* cited by examiner

*Primary Examiner* — Dennis Heyer
(74) *Attorney, Agent, or Firm* — Pai Patent & Trademark Law Firm; Chao-Chang David Pai

(57) ABSTRACT

The disclosure provides a method for treating hepatitis C, including: administering an effective amount of a proanthocyanidins oligomer to a subject in need, wherein the structure of the proanthocyanidins oligomer is shown as Formula (I):

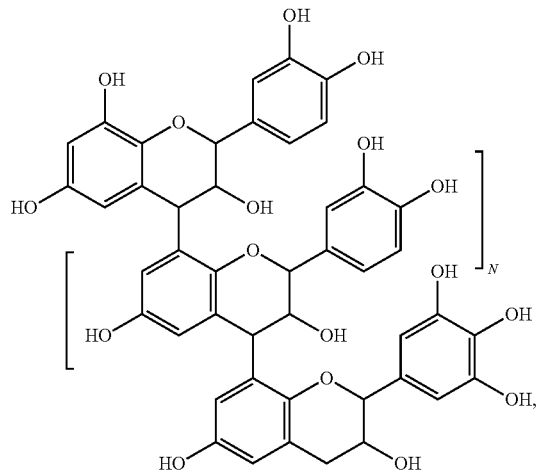

Formula (I)

and in Formula (I), N is an integer of about 1-18.

16 Claims, No Drawings

METHOD FOR TREATING HEPATITIS C

CROSS REFERENCE TO RELATED APPLICATIONS

This application is a Continuation-In-Part of pending U.S. patent application Ser. No. 12/647,496, filed Dec. 27, 2009 and entitled "Plant extract composition for treating hepatitis C" which claims priority to Taiwan Patent Application No. 097151394, filed Dec. 30, 2008, both of which are disclosed herein in their entirety.

TECHNICAL FIELD

The present invention relates to a method for treating hepatitis C, and in particular relates to a method for treating hepatitis C through administering a proanthocyanidins oligomer which is able to inhibit hepatitis C virus activity.

BACKGROUND

About 2-3% of the world population is infected by hepatitis C and the number is increasing by 3-4 million patients every year. Presently, the tested and approved anti-hepatitis C drugs are α-interferon and ribavirin that have been used to enhance the anti-hepatitis C curative effect. However, use of both drugs induces serious side effects and results in drug-resistance.

Also presently, the biochemical and pharmacodynamic activities of the proanthocyanidins have been known to comprise anti-oxidant activity, enzyme inhibition activity, anti-mutation activity, and activity for reducing capillary permeability. Also, the therapeutic effects of the proanthocyanidins are known to comprise anti-inflammation, anti-allergy and anti-ulcer and cancer prophylaxis effects, among others.

Taiwan Patent Number 1274551 discloses a nutriment containing taurine, β-carotene, proanthocyanidins extracted from grape seeds, vitamin E and vitamin C. The nutriment is found to have an effect on improving chronic hepatitis.

Accordingly, proanthocyanidins is a natural compound isolated from plants, and it has been used to improve human health. However, proanthocyanidins applied to inhibit hepatitis C viral replication has not yet been disclosed.

BRIEF SUMMARY

The disclosure provides a plant extract composition for treating hepatitis C, comprising an effective amount of the proanthocyanidins oligomer extracted from a plant material, and a pharmaceutically acceptable carrier or salt.

The disclosure further provides a method for treating hepatitis C, comprising: administering an effective amount of a proanthocyanidins oligomer to a subject in need.

A detailed description is given in the following embodiments with reference to the accompanying drawings.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure uses a composition containing proanthocyanidins oligomer extracted from plant as a drug inhibiting hepatitis C and the disclosure also uses proanthocyanidins oligomer extracted from plant as a nutriment inhibiting the activity of the hepatitis C virus. The hepatitis C replicon huh-luc/noe-ET cell was stably transfected with the I389luc-ubi-NS3-3'/ET gene and resulted in replicative capability of HCV genome. The HCV replication cell is able to express a firefly luciferase-ubiquitin-neomycin fusion protein translated by the internal ribosomal entry site (IRES) of the hepatitis C virus and is able to express the hepatitis C viral non-structural protein (NS3-5B) including protease, helicase and polymerase translated by the IRES of the encephalomyocarditis virus (EMCV). When the replication complex composed of the IRES of the hepatitis C virus or the nonstructural protein of the hepatitis C virus is influenced by a candidate, the effect of the candidate for inhibiting the activity of the hepatitis C virus repilcon is able to be estimated by determining the intensity of the firefly luciferase activity (Lohmann et al. 1999, Science. 285:110-113). This HCV replicon system has been used worldwide as new drug development tool (Bartenschlager, 2002, Nature reviews in drug discovery. 1: 911-916; Vorlijk et al. 2003, J. Virological Methods. 110: 201-209). The potential candidate to inhibit hepatitis C viral replication can be screened using above described method.

First, a composition containing proanthocyanidins oligomer or proanthocyanidins oligomer is extracted from a plant material. After numerous tests, grape seeds, *Polygonum chinense, Ampelopsis brevipedunculata* and *Ampelopsis cantoniensis* were discovered to have the anti-hepatitis C viral replication activity. After tracing of active components of the plant materials, the polar components of the extracts were found to have an abundant amount of the proanthocyanidins oligomer as the active component. Thus, the disclosure uses extraction technology to extract the parts containing the abundant proanthocyanidins (or the composition having proanthocyanidins) of the plants, to be used as an anti-hepatitis C virus drug.

In the disclosure, the dried or fresh plants were used as starting materials. The extraction procedure included crashing raw materials, de-esterification, solvent extraction, isolation and purification, concentration, granulation processes, etc. Isolation processes may comprise solvent precipitation, liquid-liquid phase extraction and isolation using resin, etc. In one embodiment, the dried or fresh plant materials may be cut into slices or pulverized and then be extracted with solvents.

The plant materials used for extraction may include grape seeds, *Polygonum chinense, Ampelopsis brevipedunculata, Ampelopsis cantoniensis* or combinations thereof. The extraction solvent may comprise a polar organic solvent or a mixture of a polar organic solvent and water. The polar organic solvent may comprise acetone, low-alkyl alcohol or ethyl acetate.

In other embodiments, extracted composition obtained from the above described process may be further dissolved in a high polar solvent, and then extracted with a low polar solvent to remove low polar impurities.

The structure of the proanthocyanidins oligomer purified from the process mentioned above is shown as Formula (I):

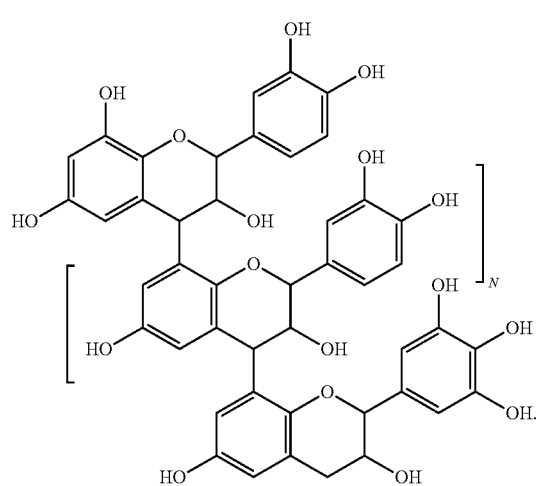

Formula (I)

In the Formula (I), N may be an integer of about 1-18.

In one embodiment, the extracted plant material may be grape seeds and a degree of polymerization of the proanthocyanidins oligomer extracted therefrom may be about 1-18. In other embodiments, the extracted plant material may be *Polygonum chinense* and a degree of polymerization of the proanthocyanidins oligomer extracted therefrom may be about 1-18. In another embodiment, the extracted plant material may be *Ampelopsis brevipedunculata* and a degree of polymerization of the proanthocyanidins oligomer extracted therefrom may be about 1-18. In another embodiment, the extracted plant material may be *Ampelopsis cantoniensis* and a degree of polymerization of the proanthocyanidins oligomer extracted therefrom may be about 1-18.

The extracted proanthocyanidins oligomer may comprise the proanthocyanidins oligomers with a single degree of polymerization, or the extracted proanthocyanidins oligomer may comprise a mixture of the proanthocyanidins oligomers with different degrees of polymerization.

It was shown that the plant material extract containing proanthocyanidins oligomers or proanthocyanidins oligomers extracted from the plant material inhibited HCV replication over 80% at 50 μg/ml. In one embodiment, the grape seed extract composition containing proanthocyanidins oligomers or proanthocyanidins oligomers extracted from the grape seeds also inhibited HCV replication over 80% at 50 μg/ml. In another embodiment, the *Polygonum chinense* extract composition containing proanthocyanidins oligomers or proanthocyanidins oligomers extracted from the *Polygonum chinense* inhibited HCV replication over 80% at 50 μg/ml.

In the disclosure, the plant material extracted composition containing proanthocyanidins oligomers or proanthocyanidins oligomers may be used to form a pharmaceutical composition for treating hepatitis C. The pharmaceutical composition may comprise the extracted proanthocyanidins oligomers mentioned above and a pharmaceutically acceptable carrier or salt.

The pharmaceutically acceptable carrier may comprise, but is not limited to, a solvent, a dispersion medium, a coating, an antibacterial and antifungal agent, or an isotonic and absorption delaying agent. The pharmaceutical composition can be formulated into dosage forms for different administration routes utilizing conventional methods.

The pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The pharmaceutical composition may be administered orally, parentally by an inhalation spray or via an implanted reservoir. The parental method may comprise subcutaneous, intracutaneous, intravenous, intramuscular, intraarticular, intraarterial, intrasynovial, intrasternal, intrathecal, and intraleaional, as well as infusion techniques.

An oral composition can comprise, but is not limited to, tablets, capsules, emulsions and aqueous suspensions, dispersions and solutions.

The disclosure further provides a method for treating hepatitis C. The method for treating hepatitis C may comprise, but is not limited to administering an effective amount of a proanthocyanidins oligomer to a subject in need, wherein the structure of the proanthocyanidins oligomer is shown as Formula (I):

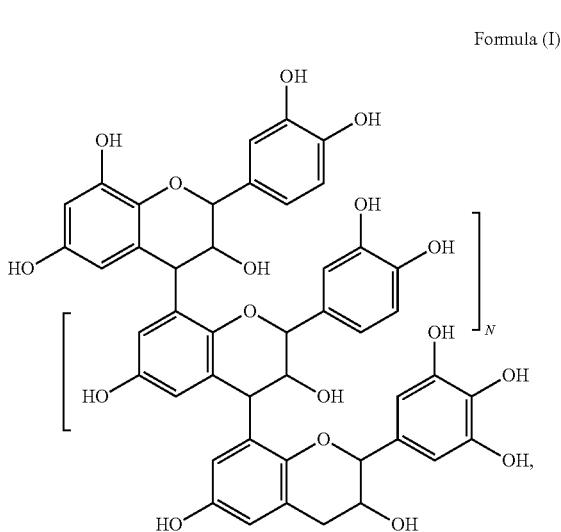 [SMILES: Oc1cc(O)c2c(c1)C(c1cc(O)cc3c1OC(c1ccc(O)c(O)c1)C(O)C3c1cc(O)cc3c1OC(c1cc(O)c(O)c(O)c1)C(O)C3)C(O)C(c1ccc(O)c(O)c1)O2]

Formula (I)

In Formula (I), N may be an integer of about 1-18.

In one embodiment, the proanthocyanidins oligomer may comprise the proanthocyanidins oligomers with a single degree of polymerization. In another embodiment, the proanthocyanidins oligomer may comprise a mixture of the proanthocyanidins oligomers with different degrees of polymerization.

In one embodiment the proanthocyanidins oligomers may inhibit HCV replication over 80% at 50 μg/ml.

The proanthocyanidins oligomer may be obtained from chemical synthesis or extracting a chemical synthesis. In one embodiment, the proanthocyanidins oligomer may be extracted from a chemical synthesis. The plant material may comprise grape seeds, *Polygonum chinense, Ampelopsis brevipedunculata, Ampelopsis cantoniensis* or combinations thereof, but is not limited thereto.

In one embodiment, the plant material mentioned above may be grape seeds and a degree of polymerization of the proanthocyanidins oligomer extracted therefrom may be about 1-18. In other embodiments, the plant material mentioned above may be *Polygonum chinense* and a degree of polymerization of the proanthocyanidins oligomer extracted therefrom may be about 1-18. In another embodiment, the plant material mentioned above may be *Ampelopsis brevipedunculata* and a degree of polymerization of the proanthocyanidins oligomer extracted therefrom may be about 1-18. In further another embodiment, the plant material mentioned above may be *Ampelopsis cantoniensis* and a degree of polymerization of the proanthocyanidins oligomer extracted therefrom may be about 1-18.

In addition, in one embodiment, a solvent used to extract the plant material may comprise a polar organic solvent or a mixture of a polar organic solvent and water. In another embodiment, a solvent used to extract the plant material may comprise acetone or a mixture of acetone and water. In another embodiment, a solvent used to extract the plant material may comprise low-alkyl alcohol or a mixture of low-alkyl alcohol and water. In another embodiment, a solvent used to extract the plant material may comprise ethyl acetate or a mixture of ethyl acetate and water.

EXAMPLE

Example 1

1 Kg of the dried *Polygonum chinense* root was dipped in 95% ethanol and shaked by 120 rpm for 3 days at room temperature to extract active components. After the extracted solution was filtered, the extract was concentrated in vacuo to a minimum. 90 g of the crude extract was dissolved/suspended into a mixture of water and ethanol (95:5) and then the mixture was sequentially partitioned with hexane, ethyl ether and ethyl acetate to afford hexane layer, ethyl ether layer, ethyl acetate layer, and residue, respectively. The extraction process is shown in the following:

The extract from *Polygonum chinense* root was mixed well with hexane, placed in a funnel and left standing for layer separation. Following layer separation, the upper layer of the mixed solution was obtained. The process was repeated for three times and the hexane layer was collected. Next, the lower layer (water layer) was mixed well with ethyl ether and placed in a funnel and left standing for layer separation. Following layer separation, the upper layer of the solution was obtained. The process was repeated for three times and an ethyl ether layer was collected. After that, the lower layer (water layer) was mixed well with ethyl acetate and placed in a funnel and left standing for layer separation. Following layer separation, the upper layer of the solution was obtained. The process was repeated for three times and an ethyl acetate layer and the water layer from the third process were obtained. Each layered solution were dried in vacuo to afford 4.6 g of hexane layer extract, 2.9 g of ethyl ether layer extract, 5.6 g of ethyl acetate layer extract and 60-70 g of water layer extract, respectively.

Four extracts were performed to determine inhibiting activity of hepatitis C virus. The test results showed that the water layer extract had the highest inhibiting activity of Hepatitis C virus. The cytotoxicity $CC_{50}$ thereof was greater than 1000 μg/ml and inhibition activity $IC_{50}$ thereof was 5.2±1.2 μg/ml. The inhibition activity $IC_{50}$ of the ethanol crude extract was 11.82±3.3 μg/ml and further extraction of the ethanol crude extract resulted in increasing 2 fold inhibition activity compared to ethanol crude extract.

TABLE 1

Inhibition test of hepatitis C viral replication activity using extracts which was extracted following with hexane, ethyl ether, ethyl acetate, water, and ethanol from the roots of *Polygonum chinense*, respectively. The original ethanol crude extract and final water layer extract were used to test anti-HCV activity in huh-luc/noe-ET cells.

| Sample | $IC_{50}$ (μg/ml) |
|---|---|
| ethanol crude extract | 11.8 ± 3.3 |
| Water layer extract | 5.2 ± 1.2 |

Table 1 showed that the water extract had the best Hepatitis C virus inhibition activity. Therefore, the water extract was selected for further purification using open-column chromatography.

Open Column Chromatography:

1.0077 g of the water layer extract was separated by open column chromatography (column packed with RP C-18/ 30.4419 g of silica; 2.2×25.3 cm) with successively changes of the mobile phase comprising a mixture of water and acetone (500 mL, water:acetone=4:1), a mixture of water and acetone (1,000 mL, water:acetone=3:1), a mixture of water and acetone (2:1), a mixture of water and acetone (1:1) and acetone. The eluents were analyzed using thin layer chromatography and combined the same constitute to obtain 10 subfractions to perform the inhibition test of hepatitis C virus. Table 2 shows the results of 6 of the 10 samples, wherein the extract from the mixture of water and acetone (3:1, fraction 126-250 ml) have inhibition activity of hepatitis C virus.

Mass spectrometry analysis was performed for proanthocyanidins oligomer extracted from *Polygonum chinense* by the methods used in examples of the disclosure.

TABLE 2

Inhibition test of hepatitis C viral replication activity using the crude and further fractionated extracts of *Polygonum chinense*.

| Sample | Activity (50 μg/ml) Inhibition (%) | Cytotoxicity $CC_{50}$ (μg/ml) |
|---|---|---|
| *Polygonum chinense* water layer extract | 39.6 ± 4.7 | 900.1 |
| *Polygonum chinense* water:acetone = 4:1 1-125 ml | 43.9 ± 5.4 | >1000 |
| *Polygonum chinense* water:acetone = 4:1 126-250 ml | 37.1 ± 5.0 | >1000 |
| *Polygonum chinense* water:acetone = 4:1 251-500 ml | 32.7 ± 8.0 | 757.5 |
| *Polygonum chinense* water:acetone = 3:1 1-125 ml | 40.6 ± 16.3 | 413.8 |
| *Polygonum chinense* water:acetone = 3:1 126-250 ml | 72.3 ± 4.4 | 269.1 |
| *Polygonum chinense* water:acetone = 3:1 251-500 ml | 13.7 ± 14.8 | >1000 |

Example 2

1. 5 g of the dried *Polygonum chinense* root was dipped in 50 ml of pure water and shaked at 120 rpm for 24 hours at room temperature to produce an extract solution. The extracts were concentrated in vacuo and 0.0676 g of the extract was used to test the inhibition activity of hepatitis C virus. The data showed that this extract can inhibit 58.7±5.9% of hepatitis C viral replication at concentration of 50 μg/ml.

2. The same process as step 1 was performed, wherein the solvent was changed to be 50 ml of acetone. 0.0043 g of the extract was used to test the inhibition activity of hepatitis C virus. The data showed that this extract can inhibit 88.7±1.3% of hepatitis C viral replication at concentration of 50 μg/ml.

3. The same process as step 1 was performed, wherein the solvent was changed to be 50 ml of a mixture of acetone and pure water (1:1). 0.0488 g of the extract was used to test the inhibition activity of hepatitis C virus. The data showed that this extract can inhibit 87.3±1.9 of hepatitis C viral replication at concentration of 50 μg/ml.

4. The same process as step 1 was performed, wherein the solvent was changed to be 50 ml of a mixture of acetone and pure water (1:2). 0.0082 g of the extract was used to test the inhibition activity of hepatitis C virus. The data showed that this extract can inhibit 79.9±2.2% of hepatitis C viral replication at concentration of 50 μg/ml.

5. The same process as step 1 was performed, wherein the solvent was changed to be 50 ml of a mixture of acetone and pure water (2:1). 0.0522 g of the extract was used to test the inhibition activity of hepatitis C virus. The data showed that this extract can inhibit 82.3±2.7% of hepatitis C viral replication at concentration of 50 μg/ml.

6. The same process as step 1 was performed, wherein the solvent was changed to be 50 ml of methanol. 0.0379 g of the extract was used to perform the hepatitis C virus activity inhibition test. For a 50 μg/ml concentration of the extract, the inhibition rate to the hepatitis C virus was 83.5±2.8%.

7. The same process as step 1 was performed, wherein the solvent was changed to be 50 ml of a mixture of methanol and pure water (1:1). 0.0435 g of the extract was used to test the inhibition activity of hepatitis C virus. The data showed that this extract can inhibit 84.0±4.6% of hepatitis C viral replication at concentration of 50 μg/ml.

8. The same process as step 1 was performed, wherein the solvent was changed to be 50 ml of a mixture of methanol and pure water (1:2). 0.0622 g of the extract was used to test the inhibition activity of hepatitis C virus. The data showed that this extract can inhibit 79.0±6.8% of hepatitis C viral replication at concentration of 50 μg/ml.

9. The same process as step 1 was performed, wherein the solvent was changed to be 50 ml of a mixture of methanol and water (2:1). 0.0272 g of the extract was used to test the inhibition activity of hepatitis C virus. The data showed that this extract can inhibit 85.0±3.4% of hepatitis C viral replication at concentration of 50 μg/ml.

10. The same process as step 1 was performed, wherein the solvent was changed to be 50 ml of ethyl acetate-saturated pure water solution. 0.0337 g of the extract was used to test the inhibition activity of hepatitis C virus. The data showed that this extract can inhibit 75.7±0.8% of hepatitis C viral replication at concentration of 50 μg/ml.

The inhibiting activities of hepatitis C virus test by using the *Polygonum chinense* root extracted with the solvents mentioned above are shown in Table 3.

TABLE 3

Inhibition test of hepatitis C viral replication activity using the root of *Polygonum chinense*, following crude and fractional extraction with various solvents and ratios.

| Root of *Polygonum chinense* | Activity (50 μg/ml) Inhibition (%) | Cytotoxicity $CC_{50}$ (μg/ml) |
| --- | --- | --- |
| water | 58.7 ± 5.9 | >333 |
| acetone | 88.7 ± 1.3 | >333 |
| acetone/water = 1:1 | 87.3 ± 1.9 | >333 |

TABLE 3-continued

Inhibition test of hepatitis C viral replication activity using the root of *Polygonum chinense*, following crude and fractional extraction with various solvents and ratios.

| Root of *Polygonum chinense* | Activity (50 μg/ml) Inhibition (%) | Cytotoxicity $CC_{50}$ (μg/ml) |
| --- | --- | --- |
| acetone/water = 1:2 | 79.9 ± 2.2 | >333 |
| acetone/water = 2:1 | 82.3 ± 2.7 | >333 |
| methonal | 83.5 ± 2.8 | >333 |
| methonal/water = 1:1 | 84.0 ± 4.6 | >333 |
| methonal/water = 1:2 | 79.0 ± 6.8 | >333 |
| methonal/water = 2:1 | 85.0 ± 3.4 | >333 |
| ethyl acetate-saturated pure water | 75.7 ± 0.8 | >333 |

Example 3

1. 5 g of the grape seeds (normal grape) was dipped in 50 ml of pure water and shaked at 120 rpm for 24 hours at room temperature to produce extract solution. The extracts were concentrated in vacuo and 0.236 g of the extract was used to test the inhibition activity of hepatitis C virus. The inhibition rate of the hepatitis C virus was 81.6±3.3% at concentration of 50 μg/ml.

2. The same process as step 1 was performed, wherein the solvent was changed to be 50 ml of acetone. 0.687 g of the extract was used to test the inhibition activity of hepatitis C virus. The inhibition rate of the hepatitis C virus was 5.0±12.2% at concentration of 50 μg/ml.

3. The same process as step 1 was performed, wherein the solvent was changed to be 50 ml of a mixture of acetone and pure water (1:1). 0.1164 g of the extract was used to test the inhibition activity of hepatitis C virus. The inhibition rate of the hepatitis C virus was 82.1±4.7% at concentration of 50 μg/ml.

4. The same process as step 1 was performed, wherein the solvent was changed to be 50 ml of a mixture of acetone and pure water (1:2). 0.034 g of the extract was used to test the inhibition activity of hepatitis C virus. The inhibition rate of the hepatitis C virus was 87.3±2.9% at concentration of 50 μg/ml.

5. The same process as step 1 was performed, wherein the solvent was changed to be 50 ml of a mixture of acetone and pure water (2:1). 0.1213 g of the extract was used to test the inhibition activity of hepatitis C virus. The inhibition rate of the hepatitis C virus was 80.4±7.9% at concentration of 50 μg/ml.

6. The same process as step 1 was performed, wherein the solvent was changed to be 50 ml of saturated ethyl acetate solution. 0.0506 g of the extract was used to test the inhibition activity of hepatitis C virus. The inhibition rate of the hepatitis C virus was 87.1±2.5% at concentration of 50 μg/ml.

The inhibition activity of hepatitis C virus test by using rape seeds extracted with the solvents mentioned above are shown in Table 4. Mass spectrometry analysis was performed for proanthocyanidins oligomer extracted from grape seeds by the methods used in examples of the disclosure

TABLE 4

Inhibition test of hepatitis C viral replication activity using the crude and fractionated extracts of grape seeds.

| Grape seeds (normal grape) | Activity (50 μg/ml) Inhibition (%) | Cytotoxicity $CC_{50}$ (μg/ml) |
|---|---|---|
| water | 81.6 ± 3.3 | >333 |
| acetone | 5.0 ± 12.2 | >333 |
| acetone/water = 1:1 | 82.1 ± 4.7 | >333 |
| acetone/water = 1:2 | 87.3 ± 2.9 | >333 |
| acetone/water = 2:1 | 80.4 ± 7.9 | >333 |
| ethyl acetate-saturated pure water | 87.1 ± 2.5 | >333 |

Example 4

1. 5 g of the flesh of the *Ampelopsis brevipedunculata* was dipped in 50 ml of water and shaken at 120 rpm for 24 hours at room temperature to produce an extract solution. The extracts were concentrated in vacuo and 0.0175 g of the extract was used to test the inhibition activity of hepatitis C virus. The inhibition rate of the hepatitis C virus was 84.7±1.7% at concentration of 50 μg/ml.

2. The same process as step 1 was performed, wherein the solvent was changed to be 50 ml of methanol. 0.0474 g of the extract was used to test the inhibition activity of hepatitis C virus. The inhibition rate of the hepatitis C virus was 92.1±0.7% at concentration of 50 μg/ml.

3. The same process as step 1 was performed, wherein the solvent was changed to be 50 ml of a mixture of methanol and pure water (1:1). 0.0279 g of the extract was used to test the inhibition activity of hepatitis C virus. The inhibition rate of the hepatitis C virus was 92.1±1.2% at concentration of 50 μg/ml.

4. The same process as step 1 was performed, wherein the solvent was changed to be 50 ml of a mixture of methanol and pure water (1:2). 0.0674 g of the extract was used to test the inhibition activity of hepatitis C virus. The inhibition rate of the hepatitis C virus was 92.7±0.3% at concentration of 50 μg/ml.

5. The same process as step 1 was performed, wherein the solvent was changed to be 50 ml of a mixture of methanol and pure water (2:1). 0.0536 g of the extract was used to test the inhibition activity of hepatitis C virus. The inhibition rate of the hepatitis C virus was 90.0±2.5% at concentration of 50 μg/ml.

6. The same process as step 1 was performed, wherein the solvent was changed to be 50 ml of ethyl acetate-saturated pure water solution. 0.0408 g of the extract was used to test the inhibition activity of hepatitis C virus. The inhibition rate of the hepatitis C virus was 91.3±0.7% at concentration of 50 μg/ml.

The inhibition activity of hepatitis C virus test by using grape seeds extracted with the solvents mentioned above are shown in Table 5.

TABLE 5

Inhibition test of hepatitis C viral replication activity using the crude and fractionated extracts of *Ampelopsis brevipedunculata*.

| *Ampelopsis brevipedunculata* | Activity (50 μg/ml) Inhibition (%) | Cytotoxicity $CC_{50}$ (μg/ml) |
|---|---|---|
| water | 84.7 ± 1.7 | >1000 |
| methanol | 92.1 ± 0.7 | >1000 |
| methanol/water = 1:1 | 92.1 ± 1.2 | >1000 |
| methanol/water = 1:2 | 92.7 ± 0.3 | >1000 |
| methanol/water = 2:1 | 90.0 ± 2.5 | >1000 |
| ethyl acetate-saturated pure water | 91.3 ± 0.7 | >1000 |

Example 5

100 g of the dried *Ampelopsis cantoniensis* was dipped in 95% ethanol and shaked at 120 rpm for 3 days at room temperature to produce extract solution. The extract solution was concentrated in vacuo and used to test the inhibition activity of hepatitis C virus. The inhibition rate of the hepatitis C virus was 72-80% at concentration of 50 μg/ml.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for inhibiting hepatitis C viral replication, comprising:
   administering an effective amount of a proanthocyanidins oligomer alone to a subject in need, wherein the proanthocyanidins oligomer has inhibition activity of hepatitis C viral replication, and the structure of the proanthocyanidins oligomer is shown as Formula (I):

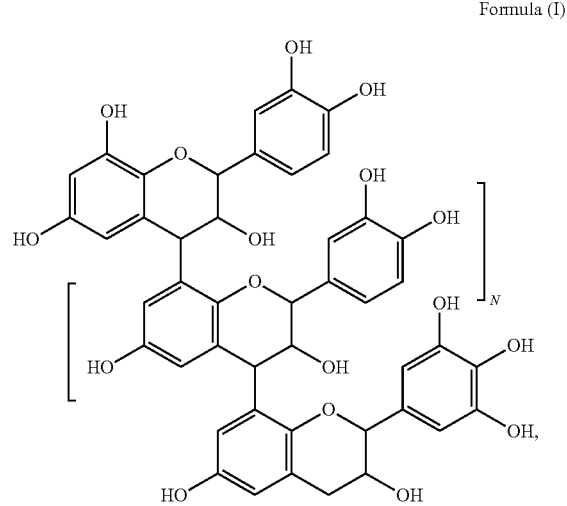 [SMILES: Oc1cc(O)c2c(c1)C(c1cc(O)cc3c1OC(c1ccc(O)c(O)c1)C(O)C3c1cc(O)cc3c1OC(c1cc(O)c(O)c(O)c1)C(O)C3)C(O)C(c1ccc(O)c(O)c1)O2]

Formula (I)

and wherein N is an integer of about 1-18.

2. The method for inhibiting hepatitis C viral replication as claimed in claim 1, wherein the proanthocyanidins oligomer comprises the proanthocyanidins oligomers with a single degree of polymerization or a mixture of the proanthocyanidins oligomers with different degrees of polymerization.

3. The method for inhibiting hepatitis C viral replication as claimed in claim 1, wherein the proanthocyanidins oligomer is extracted from a plant material.

4. The method for inhibiting hepatitis C viral replication as claimed in claim 3, wherein the plant material comprises grape seeds, *Polygonum chinense, Ampelopsis brevipedunculata, Ampelopsis cantoniensis* or combinations thereof.

5. The method for inhibiting hepatitis C viral replication as claimed in claim 4, wherein the plant material comprises grape seeds.

6. The method for inhibiting hepatitis C viral replication as claimed in claim 5, wherein the degree of polymerization of the proanthocyanidins oligomer is about 1-18.

7. The method for inhibiting hepatitis C viral replication as claimed in claim 3, wherein the plant material comprises *Polygonum chinense*.

8. The method for inhibiting hepatitis C viral replication virus as claimed in claim 7, wherein the degree of polymerization of the proanthocyanidins oligomer is about 1-18.

9. The method for inhibiting hepatitis C viral replication as claimed in claim 3, wherein the plant material comprises *Ampelopsis brevipedunculata*.

10. The method for inhibiting hepatitis C viral replication as claimed in claim 9, wherein the degree of polymerization of the proanthocyanidins oligomer is about 1-18.

11. The method for inhibiting hepatitis C viral replication as claimed in claim 3, wherein the plant material comprises *Ampelopsis cantoniensis*.

12. The method for inhibiting hepatitis C viral replication as claimed in claim 11, wherein the degree of polymerization of the proanthocyanidins oligomer is about 1-18.

13. The method for inhibiting hepatitis C viral replication as claimed in claim 3, wherein a solvent used to extract the plant material comprises a polar organic solvent or a mixture of a polar organic solvent and water.

14. The method for inhibiting hepatitis C viral replication as claimed in claim 3, wherein a solvent used to extract the plant material comprises acetone or a mixture of acetone and water.

15. The method for inhibiting hepatitis C viral replication as claimed in claim 3, wherein a solvent used to extract the plant material comprises low-alkyl alcohol or a mixture of low-alkyl alcohol and water.

16. The method for inhibiting hepatitis C viral replication as claimed in claim 3, wherein a solvent used to extract the plant material comprises ethyl acetate or a mixture of ethyl acetate and water.

* * * * *